United States Patent [19]

Park et al.

[11] Patent Number: 6,136,850
[45] Date of Patent: Oct. 24, 2000

[54] METHODS AND COMPOSITIONS FOR INHIBITING DEPOSIT FORMATION ON CONTACT LENSES

[75] Inventors: John Y. Park, Santa Ana; James N. Cook, Mission Viejo; Dorla Mirejovsky, Irvine; Steven S. Matsumoto, San Clemente, all of Calif.

[73] Assignee: Allergan, Waco, Tex.

[21] Appl. No.: 08/016,931

[22] Filed: Feb. 12, 1993

Related U.S. Application Data

[63] Continuation-in-part of application No. 07/698,611, May 10, 1991, abandoned.

[51] Int. Cl.[7] ........................ A61K 31/355; A61K 31/34; A61K 31/07
[52] U.S. Cl. .......................... 514/458; 514/474; 514/725; 514/912
[58] Field of Search ............................. 514/19, 912, 369, 514/458, 554, 474, 725

[56] References Cited

U.S. PATENT DOCUMENTS

| | | |
|---|---|---|
| Re. 32,672 | 5/1988 | Huth et al. . |
| 3,482,025 | 12/1969 | Murakami et al. . |
| 3,910,296 | 10/1975 | Karageozian et al. . |
| 4,070,483 | 1/1978 | Lerman . |
| 4,285,738 | 8/1981 | Ogata . |
| 4,411,932 | 10/1983 | Kwan . |
| 4,443,432 | 4/1984 | Garabedian et al. . |
| 4,459,309 | 7/1984 | Chiou . |
| 4,546,123 | 10/1985 | Schafer et al. . |
| 4,550,022 | 10/1985 | Garabedian et al. . |
| 4,559,343 | 12/1985 | Han et al. . |
| 4,609,493 | 9/1986 | Schafer . |
| 4,613,379 | 9/1986 | Su et al. . |
| 4,618,669 | 10/1986 | Decreu et al. . |
| 4,690,773 | 9/1987 | Ogunbiyi et al. . |
| 4,710,313 | 12/1987 | Miyajima et al. . |
| 4,715,899 | 12/1987 | Chanda et al. . |
| 4,734,475 | 3/1988 | Goldenberg et al. . |
| 4,738,790 | 4/1988 | Miyajima et al. . |
| 4,749,511 | 6/1988 | Lad et al. . |
| 4,771,126 | 9/1988 | Hirotsuka et al. . |
| 4,784,685 | 11/1988 | Meister . |
| 4,837,021 | 6/1989 | Andermann et al. . |
| 4,879,370 | 11/1989 | Meister . |

FOREIGN PATENT DOCUMENTS 60-254114  12/1985  Japan .

OTHER PUBLICATIONS

Bendazac Lysine In The Treatment Of Cataract, Brown et al, Clinical, Apr. 29, 1988.
Studies on the Mechanism of Action of Bendazac (AF 983), Silvestrini et al, Arzuema–Forsch (Drug Res.) Jahrgang 20–Nr. 2 (1970).
Abstract of Japanese Patent Application JP–196378, 1991.
Abstract of Japanese Application JP–011479, 1991.

*Primary Examiner*—Zohreh Fay
*Attorney, Agent, or Firm*—Stout, Uxa, Buyan & Mullins, LLP; Frank J. Uxa

[57] ABSTRACT

Methods and compositions for inhibiting the formation of proteinaceous and/or lipid deposits on a contact lens are disclosed. In one embodiment, the present method comprises contacting a contact lens being worn in a mammalian eye with at least one ophthalmically acceptable antioxidant component in an amount effective to inhibit the formation of at least one of proteinaceous deposits and lipid deposits on the contact lens in the eye.

18 Claims, No Drawings

METHODS AND COMPOSITIONS FOR INHIBITING DEPOSIT FORMATION ON CONTACT LENSES

RELATED APPLICATION

This application is a continuation-in-part of application Ser. No. 07/698,611 filed May 10, 1991 now abandoned. This prior application is incorporated in its entirety by reference herein.

BACKGROUND OF THE INVENTION

This invention relates to methods and compositions for inhibiting deposit formation on contact lenses. More particularly, the invention relates to methods and compositions for inhibiting the formation of proteinaceous deposits and/or lipid deposits on contact lenses being worn in mammalian, preferably human, eyes.

The use of contact lenses for vision correction is widespread and provides substantial advantages. However, one problem that is apparent is the lack of comfort in wearing contact lenses over long periods of time, even though the lenses themselves are removed from the eye on a regular and frequent basis. One reason for this eye discomfort and irritation is the formation of deposit material on the contact lenses during wear. Such deposit material, which often has its origin in proteinaceous and/or lipid material from the eye of the contact lens wearer, becomes deposited on the contact lens and creates irregularities on the surface of the lens which tend to cause eye discomfort and/or irritation.

One approach to removing the deposit material from a contact lens is to clean the lens of such deposit material while the lens is outside of the eye and not in use. Examples of this "outside the eye" cleaning approach are set forth in Chanda et al U.S. Pat. No. 4,715,899 and Ogata U.S. Pat. No. 4,285,738. Chanda et al teaches the concurrent use of an aqueous solution containing an inactivated sulfhydryl protease (an enzyme) and an aqueous thiol reducing agent, such as glutathione, to remove protein soil from contact lenses outside the eye. Ogata et al teaches removing proteinaceous material from contact lenses outside the eye by immersing the lenses in an aqueous hypotonic composition including urea or a salt of guanidine and a reducing agent, such as glutathione. Neither of these patents even suggest using these compositions in the eye. The enzyme-containing composition of Chanda et al and the protein denaturant-containing, hypotonic composition of Ogata et al are not ophthalmically acceptable and may even cause substantial ocular damage if placed in the eye.

The approach of removing proteinaceous deposit material from a contact lens outside the eye, although very useful, does require an additional step to be implemented by the wearer of the contact lens. It would be advantageous to provide a system whereby the formation of deposit material on a contact lens is inhibited during use of the contact lens.

Removing already formed deposit material from a contact lens is an entirely different phenomenon from inhibiting the formation of deposit material on a contact lens. An agent known to be useful in removing already formed deposit material is not obviously effective in inhibiting the formation of such deposit material in the first place. This is particularly true if the deposit removal is to be effected outside the eye and the inhibition of deposit formation is to occur while the lens is being worn in the eye.

Of course, any components or materials which are to be used while the contact lens is in the eye must be ophthalmically acceptable. By "ophthalmically acceptable" is meant that a material has substantially no detrimental effect on the mammalian eye into which it is placed.

Japanese patent application JP-196378 discloses an eye lotion useful as a remedy for cataract. The lotion contains oxidized glutathione as a prodrug for reduced glutathione which plays a role in maintaining transparency of the natural crystalline lens. This patent application does not disclose any effect of the eye lotion on the wearing of contact lenses.

Japanese patent application JP-011497 discloses ophthalmic compositions for treatment of corneal diseases which contain oxidized form glutathione or its salts as principal components. These compositions are disclosed as having a pH which is adjusted at 5.0 and as being useful for the treatment of corneal diseases, e.g., keratitis. This application teaches that conventional auxiliaries may be added, for example, polyvinyl alcohol as a thickener. This application does not teach or suggest any effective use of such compositions in contact lens care.

Garabedian et al U.S. Pat. No. 4,443,432 discloses a stable sterile two part system for preparing an ocular irrigating solution for irrigating the eye during surgery. Part A involves a basic solution containing bicarbonate ion. Part B includes an acidic solution containing calcium ions, magnesium ions, dextrose and glutathione provided that one of the solutions contains sodium, potassium and chloride ions. This patent does not teach or suggest such compositions as being effective for any purpose in the contact lens care context.

Schachar U.S. Pat. No. 4,620,979 discloses a method for maintaining normal ascorbate levels in ocular tissue of an eye subjected to intraocular surgery which involves irrigating the eye with a composition comprising sodium chloride, potassium chloride, calcium chloride, magnesium chloride hydrate, sodium hydrogen phosphate, sodium dihydrogen phosphate, sodium bicarbonate, glucose, adenosine, glutathione, sodium acetate, sodium citrate, sodium lactate and ascorbate. This patent does not teach or suggest any effective use of this composition in the contact lens care context.

There continues to be a need for a system useful to inhibit the formation of deposits on contact lenses, particularly while the lenses are being worn in the eyes.

SUMMARY OF THE INVENTION

New methods and compositions for inhibiting deposit formation on contact lenses have been discovered. These methods and compositions are very effective for inhibiting the formation of proteinaceous deposits and/or lipid deposits on contact lenses being worn in mammalian, preferably human, eyes. Thus, this inhibiting effect occurs while the lens is in use in the mammalian eye. Thus, this inhibiting effect is entirely different and distinct from the removal of already formed contact lens deposit material which is accomplished while the lens is outside the eye. The present methods and compositions preferably also include one or more components which act on the contact lens to enhance the wearability of the lens, thus making it yet more comfortable for the lens wearer. The present compositions are ophthalmically acceptable, preferably substantially isotonic, and are easily used to provide an effective amount of the composition to achieve the desired deposit formation inhibiting effect.

In one embodiment, the present methods for inhibiting the formation of proteinaceous deposits and/or lipid deposits on a contact lens comprise contacting the contact lens being worn in a mammalian eye with an ophthalmically acceptable antioxidant component in an amount effective to inhibit the formation of proteinaceous deposits and/or lipid deposits on the contact lens. As used herein, the term "antioxidant component" is used to describe components which are, or can be, classified as reducing agents and/or antioxidants.

The present compositions comprise an ophthalmically acceptable carrier component; an ophthalmically acceptable wearability component in an amount effective to act, for example, on a contact lens being worn in a mammalian eye, so as to enhance the wearability of the contact lens; and an ophthalmically acceptable antioxidant component in an amount effective to inhibit the formation of at least one of proteinaceous deposits and lipid deposits on a contact lens being worn in a mammalian eye.

The present methods and compositions provide for very useful and effective inhibition of contact lens deposit formation. Moreover, the present invention can be very conveniently employed by a contact lens wearer. For example, the present compositions can be conveniently topically applied to, introduced into, the eye wearing a contact lens to provide the desired deposit formation inhibition.

DETAILED DESCRIPTION OF THE INVENTION

The present invention is applicable to all types of contact lenses on which proteinaceous deposits and/or lipid deposits tend to form during use in a mammalian eye. Such lenses, e.g., conventional soft contact lenses, RGPs and hard contact lenses, may be made of any suitable material or combination of materials and may have any suitable configuration.

One of the important features of the present invention is the use of an ophthalmically acceptable antioxidant component. It has been found that such antioxidant components are effective to inhibit the formation of at least one of proteinaceous deposits and lipid deposits on a contact lens being worn in a mammalian eye. Without wishing to limit the invention to any particular theory of operation, it is believed that the antioxidant component acts to effectively interrupt or disrupt the formation of the proteinaceous and/or lipid deposit material prior to it being deposited on the contact lens being worn. This feature of the present invention, that is the inhibition of deposit formation on a contact lens being worn in the eye, is very much different and distinct from removing deposits from contact lenses outside the eye.

In one embodiment, the present invention involves methods for inhibiting the formation of deposits on a contact lens being worn in a mammalian eye. These methods comprise contacting this contact lens with an ophthalmically acceptable antioxidant component in an amount effective to inhibit the formation of at least one proteinaceous deposits and lipid deposits on the contact lens. Any suitable ophthalmically acceptable antioxidant component may be utilized in the present invention, provided that it functions as described herein and has no substantial detrimental effect on the contact lens being worn or on the eye or person of the mammal wearing the contact lens. Preferably, the antioxidant component is soluble in the presently useful compositions. In general, the antioxidant components include ophthalmically acceptable antioxidant compounds themselves, ophthalmically acceptable antioxidant salts of such compounds, ophthalmically acceptable antioxidant derivatives of such compounds, precursors of such compounds and mixtures thereof. As used herein, the term "precursors" refers to ophthalmically acceptable materials which are converted in the eye to one or more ophthalmically acceptable antioxidant compounds (or the identified antioxidant compounds), ophthalmically acceptable antioxidant salts of antioxidant compounds (or salts of the identified antioxidant compounds), ophthalmically acceptable antioxidant derivatives of antioxidant compounds (or derivatives of the identified antioxidant compounds) and mixtures thereof.

Examples of useful antioxidant components include Vitamin A (retinol), Vitamin E (alpha-tocopherol), ascorbic acid, thiol components, ophthalmically acceptable antioxidant salts thereof, ophthalmically acceptable antioxidant derivatives thereof, precursors thereof and mixtures thereof and the like.

Examples of useful thiol components include glutathione (GSH), oxidation-type glutathione or oxidized glutathione (GSSG), N-acetylcysteine, thioctic acid, 2-oxo-thiazolidine-4-carboxylic acid, cysteine, glutamylcysteine, ethanethiol, 1,4-butanethiol, 2-mercaptoethylether, pentaerythretoltetrathiopropionate and acetate, polyethyleneglycolimercaptoacetate and methylthioglycolate, allyl mercaptan, 2-mercaptoethanol, 3-mercaptopropanol, 4-mercaptobutanol, 1-thioglycerol, thioerythritol, 2,3-dimercaptopropanol, pentaerythretolmono (di; tri) thiopropionate or acetate, thioglycolic acid, thioacetic acid, 3-mercaptopropionic acid, thiolactic acid, thiomalic acid, thiosuccinic acid, thiosalicylic acid, thiobenzoic acid and their respective water soluble salts, furfuryl mercaptan, 2-mercaptobenzimidazole, 2-mercaptobenzoxazole, 2-mercapto-3-pyridinol, dimethylaminopropanethiol, 2-mercaptoethylamine, 2-n-butylaminoethanethiol, and the like and mixtures thereof.

In one useful embodiment, the thiol component is selected from N-acetylcysteine, thioctic acid, 2-oxo-thiazolidine-4-carboxylic acid, cysteine, glutamylcysteine and mixtures thereof.

Preferably, the ophthalmically acceptable thiol component is selected from the group consisting of GSH, ophthalmically acceptable salts of GSH, GSSG, ophthalmically acceptable salts of GSSG, precursors thereof and mixtures thereof, more preferably selected from the group consisting of GSH, GSSG, ophthalmically acceptable salts thereof and mixtures thereof and still more preferably from GSH, GSSG and mixtures thereof, especially GSH.

Examples of ophthalmically acceptable anions included in the presently useful ophthalmically acceptable salts useful as antioxidant components include chloride, bromide, iodide, sulfate, bisulfate, phosphate, acid phosphate, nitrate, acetate, maleate, fumarate, oxalate, lactate, tartrate, citrate, gluconate, saccharate, p-toluene sulfonate and the like. Ophthalmically acceptable derivatives useful as antioxidant components include esters, acids and the like.

The presently useful ophthalmically acceptable antioxidant components are preferably present in an amount in the range of about 0.0001% to about 10%, more preferably about 0.001% to about 0.5%, by weight per volume of ophthalmically acceptable medium or carrier. The ophthalmically acceptable antioxidant component may be conveniently used in the form of a composition including an ophthalmically acceptable, preferably a substantially isotonic, medium or carrier, such as in the form of an artificial tear, an eye drop, a lotion which is topically applied to the eye and the like.

In one particularly useful embodiment, the present method further comprises introducing or instilling a composition, such as described herein, including an ophthalmically acceptable antioxidant component into the mammalian eye wearing the contact lens. For example, an eye drop or drops containing an effective amount of an ophthalmically acceptable antioxidant component may be added to the contact lens-wearing eye one or more times a day, in particular at the time the contact lens is present in the eye, so as to inhibit the formation of proteinaceous deposits and/or lipid deposits on the contact lens being worn.

The compositions of the present invention include an ophthalmically acceptable medium or carrier, preferably an ophthalmically acceptable liquid aqueous medium. This medium may act as a solvent for the other components in the composition. One particularly useful ophthalmically acceptable carrier is water, such as purified water, sterilized water or preserved water. The medium or carrier, and the entire composition, are preferably substantially isotonic.

One or more additional components can be included in the present compositions based on the particular application for which the compositions are formulated. Thus, the present compositions can be formulated as contact lens wetting compositions, contact lens conditioning compositions, contact lens soaking/storage compositions (for use with the lens before and/or after lens wear to condition the lens for comfort and inhibition of deposit formation) artificial tear compositions and the like. Soaking a contact lens, before and/or after lens wear, in the present compositions for a period of time, on the order of at least about 0.5 or about 1 hour, is effective to enhance the wearability of the lens and/or inhibit deposit formation on the lens after the soaked lens is placed in the eye for a period to wear.

In a particularly useful embodiment, the present compositions have a pH of greater than 5.0, preferably up to about 7.0 or about 8.0. A pH of about 5.3 to about 6.0 and preferably about 5.5 to about 5.8 is particularly useful when the antioxidant component comprises one or more forms of glutathione. The present compositions having pHs as described herein have been found to be very effective in inhibiting proteinaceous and/or lipid deposit formation on the contact lens in the eye while, at the same time, being suitable for use within the eye without adversely affecting ocular health or causing eye irritation or discomfort. Compositions having lower pH values have a tendency to cause irritation and/or discomfort in a healthy mammalian eye. To stabilize or maintain the composition at the desired pH, an effective amount of at least one buffer component may be included in the composition. The effective amount of buffer component employed to buffer or maintain the formulation at the desired pH can vary widely and depends to a large degree on the particular buffer component employed, as well as the chemical make-up of the composition. However, desirable results have been obtained when the amount of buffering component incorporated into the composition to stabilize the composition at the desired pH is in the range of about 0.005 to about 1 weight/volume percent of the composition.

Any suitable buffer component can be employed which is compatible with the other ingredients of the composition, and which does not have deleterious or toxic properties which could harm the eye or the contact lens being worn. Examples of suitable ophthalmically acceptable buffer components include acetate buffers, citrate buffers, phosphate buffers, borate buffers and mixtures thereof. Specific buffer components useful in the present invention include boric acid, sodium borate, sodium phosphates, including mono, di- and tri-basic phosphates, such as sodium phosphate monobasic monohydrate and sodium phosphate dibasic heptahydrate, and mixtures thereof. It should be noted that any other suitable ophthalmically acceptable buffer components can be employed to maintain the pH of the ophthalmic composition so that the composition is provided with an acceptable pH, and the before-mentioned buffer components are merely examples of such buffer components.

When it is determined that the composition does not have the desired pH value, the pH of the composition can be adjusted by the addition of an effective amount of either a base or an acid, as the case may be. Any suitable base or acid can be employed to adjust the pH of the composition which does not provide the composition with toxic or deleterious properties which could harm either the contact lens or the eye. An example of a base which can be used to adjust the pH of the composition is 1 N sodium hydroxide; and an example of an acid which can be used to adjust the pH of the composition is 1 N hydrochloric acid.

The present compositions preferably include an ophthalmically acceptable, preferably polymeric, wearability component in an amount effective to act, for example, on a contact lens being worn in a mammalian eye, so as to enhance the wearability of the contact lens in the mammalian eye. Such wearability components may wet (or rewet) the lens, condition the lens, coat the lens or otherwise interact with the lens to provide the wearer of the lens with an increased degree of lens wearing comfort when present in an eye wearing a contact lens relative to wearing the contact lens in the absence of the wearability component. The wearability component is preferably a polymeric component, that is, a component which has one or more sub-molecular units which are repeated at least once, preferably at least about 10 times, in each molecule of the polymeric component.

Among the useful wearability components which may be included in the present compositions are contact lens wetting (or rewetting) agents (or surfactants), contact lens conditioning agents and the like and mixtures thereof. Many such agents are conventional and well known in the art of contact lens care.

Useful contact lens wetting (or rewetting) agents (or surfactants) and conditioning agents include, but are not limited to, polyvinyl alcohol, polyoxamers (for example, polyoxyethylene, polyoxypropylene block polymers), polyvinyl pyrrolidine, hydroxypropyl methyl cellulose, hydroxyethyl cellulose, other ophthalmically acceptable cellulose derivatives, propylene glycol alginate, xanthan gum, alkyl polyglycosides, hydrolyzed wheat protein, hydrolyzed soy protein, and the like and mixtures thereof. Particularly useful as wearability components in the present invention include an ophthalmically acceptable surfactant, such as the polyoxyethylene, polyoxypropylene block polymers, and an ophthalmically acceptable conditioning component, such as propylene glycol alginate. A combination of polyvinyl alcohol and polyvinyl pyrrolidone can advantageously be employed to enhance the wearability of the contact lens in the eye.

The wearability component or components are included in the present compositions in an amount effective to impart or provide the desired increase in lens wearability. Such amount or amounts may vary widely depending, for example, on the specific composition being employed, the specific wearability component or components being utilized, the specific wearability result desired and the composition of the contact lens with which the composition is to be utilized. Preferably, the wearability component is present in an amount in the range of about 0.01% or about 0.1% to about 4%, more preferably about 0.3% to about 3%, (weight/volume) of the composition.

Further, one or more additional components may be included in the present compositions to impart or provide at least one beneficial or desired property to the compositions. Such additional components may be selected from components which are conventionally used in one or more contact lens care compositions, in particular in-the-eye contact lens care compositions. Examples of such additional components include tonicity agents, corneal nutrient agents and the like. These additional components are each included in the present compositions in an amount effective to impart or provide the beneficial or desired property to the compositions. For example, such additional components may be included in the present compositions in amounts similar to the amounts of such components used in other, e.g., conventional, in-the-eye contact lens care products.

Useful tonicity adjustors include, but are not limited to, sodium chloride, potassium chloride, mannitol, dextrose, glycerin, propylene glycol and mixtures thereof. Such tonicity adjusting components are preferably included in an amount effective to provide the desired tonicity to the composition, preferably an osmolality of at least about 200 mOsmol/kg and more preferably about 250 to about 350 or 400 mOs mol/kg. Preferably the present compositions are substantially isotonic.

Useful viscosity builders include, but are not limited to, hydroxyethyl cellulose, hydroxypropyl methyl cellulose, polyvinyl pyrrolidone, polyvinyl alcohols and mixtures thereof.

Useful corneal nutrient agents include, but are not limited to, dextrose, lactose, glutaric acid, lactic acid, other ophthalmically acceptable carbohydrates and carbohydrate derivatives, glutamine, glutamic acid, other ophthalmically acceptable amino acids, and the like and mixtures thereof.

The present compositions can be prepared in any conventional manner, such as by blending or combining the appropriate ingredients together.

The present compositions are preferably substantially free of effective amounts of one or more ionic surfactants, that is, cationic surfactants, anionic surfactants and/or amphoteric surfactants. Such ionic surfactants may adversely impact the parameters of the contact lens and/or the eye in which the contact lens is worn. Also, the present compositions are preferably substantially free of effective amounts of one or more enzymes, particularly when such compositions are to be applied directly to or in the eye.

The present compositions are particularly effective when applied directly to or in an eye, in particular an eye wearing a contact lens. Thus, the present compositions can be introduced into the eye periodically on a routine basis or on a predetermined schedule. Alternately, the compositions may be used, as needed, to inhibit proteinaceous and/or lipid deposit formation on a contact lens being worn in a mammalian eye.

The following non-limiting examples illustrate certain aspects of the present invention.

EXAMPLES 1 TO 8

A series of tests were conducted to determine the effect of glutathione (GSH) on the formation of lysozyme deposits on a contact lens.

Each of these tests was conducted using a conventional soft hydrogel contact lens (having a water constant of about 55% by weight). The lens was placed in a glass vial with 5 ml of an aqueous solution containing 1.00 g/l of lysozyme, with and without other components as shown in the table below. Following a standard in-vitro procedure for the lysozyme coating of contact lenses, the lens/solution combination was heated to 80° C. and maintained at this temperature for 60 minutes. Afterwards, the lens/solution combination was cooled to room temperature. The lens was removed from the solution and inspected using a fiber optic illuminator and an ultraviolet light spectrometer set at 280 nm to determine the extent of lysozyme deposition.

Results of these tests were as follows:

| Example | GSH, mg/l | Glycerol, mg/l | Lysozyme Fiber Optic Illuminator[1] | Deposition UV Absorbance[2] |
|---|---|---|---|---|
| 1 | 25 | 25 | None | 0.077 |
| 2 | 25 | 0 | None | 0.102 |
| 3(Comparative) | 0 | 25 | Heavy | 0.817 |
| 4 | 25 | 100 | Very Light | 0.095 |
| 5(Comparative) | 0 | 100 | Heavy | 0.787 |
| 6(Comparative) | 0 | 0 | Heavy | 0.783 |
| 7 | 5 | 0 | Very Light | 0.427 |
| 8 | 50 | 0 | Very Light Pitch Near Center (Otherwise None) | 0.130 |

[1]These results are visual observations using a fiber optic illuminator.
[2]The degree of UV absorbance increases as the amount of lysozyme deposited increases.

These results demonstrate that glutathione (GSH) is effective in inhibiting the deposition of lysozyme, which is denatured by the above-noted heating step, on contact lenses. The denatured lysozyme is a proteinaceous material which is readily deposited on contact lenses in the absence of GSH (Examples 3, 5 and 6). With glutathione (GSH) present, Examples 1, 2, 4, 7 and 8, the amount of denatured lysozyme deposited is substantially reduced. The presence of glycerol has little or no effect on the degree of denatured lysozyme deposition on the contact lens.

EXAMPLE 9

An artificial tear formulation is prepared and has the following composition:

| | |
|---|---|
| Glutathione (GSH) | 0.5% by weight |
| Polyvinyl alcohol (20–90 grade) | 1.4% by weight |
| Polyvinylpyrrolidone | 0.6% by weight |
| Sodium Chloride | 0.8% by weight |
| Hydrochloric acid | as needed to a |
| Sodium Hydroxide | pH of 5.5 to 5.8 |
| Purified Water | as needed to make volume |

This formulation is applied in the form of drops to the eyes of a human wearer of soft hydrogel contact lenses. The drops are applied twice a day, always when the contact lenses are being worn. The lenses are also subjected to frequent, conventional enzymatic cleaning when they are not being worn. Over a period of time, the lens wearer experiences substantially no discomfort and substantially no irritation as the result of contact lens wear.

While this invention has been described with respect to various specific examples and embodiments, it is to be understood that the invention is not limited thereto and that it can be variously practiced within the scope of the following claims.

What is claimed is:

1. A method for inhibiting the formation of deposits on a contact lens comprising:

introducing into a mammalian eye wearing a contact lens an ophthalmically acceptable composition comprising an ophthalmically acceptable antioxidant component in an amount effective to inhibit the formation of at least one of proteinaceous deposits and lipid deposits on said contact lens.

2. The method of claim 1 wherein said ophthalmically acceptable antioxidant component is selected from the group consisting of Vitamin A, Vitamin E, ascorbic acid, thiol components, ophthalmically acceptable antioxidant salts thereof, ophthalmically acceptable antioxidant derivatives thereof, precursors thereof and mixtures thereof.

3. The method of claim 1 wherein said ophthalmically acceptable antioxidant component is selected from the group consisting of glutathione, oxidation-type glutathione, opthalmically acceptable salts thereof and mixtures thereof.

4. The method of claim 1 wherein said ophthalmically acceptable antioxidant component is glutathione.

5. The method of claim 1 wherein said introducing step is repeated prior to removing said contact lens from said mammalian eye.

6. The method of claim 1 wherein said ophthalmically acceptable composition further includes an opthalmically acceptable aqueous carrier component and has an opthalmically acceptable pH of greater than 5.0.

7. The method of claim 6 wherein said ophthalmically acceptable composition further includes at least one additional component in an amount effective to act to enhance the wearability of said contact lens.

8. The method of claim 6 wherein said ophthalmically acceptable composition includes a combination of a surfactant component and a conditioning component, said combination being present in an amount to enhance the wearability of said contact lens.

9. The method of claim 7 wherein said ophthalmically acceptable composition is free of enzymes and ionic surfactants, and is substantially isotonic.

10. A method for inhibiting proteinaceous deposits on a contact lens comprising:

introducing into a mammalian eye wearing a contact lens a composition having an ophthalmically acceptable pH of greater than 5.0 and comprising an ophthalmically acceptable aqueous carrier component, an ophthalmically acceptable wearability component in an amount effective to act to enhance the wearability of said contact lens, an ophthalmically acceptable tonicity adjusting component in an amount effective to provide the desired tonicity to said composition, and an ophthalmically acceptable antioxidant component in an amount effective to inhibit the formation of proteinaceous deposits on said contact lens, said composition being ophthalmically acceptable, substantially isotonic and free of enzymes.

11. The method of claim 10 wherein said ophthalmically acceptable wearability component includes a combination of an opthalmically acceptable surfactant component and an opthalmically acceptable conditioning component.

12. A method for conditioning a contact lens comprising:

soaking a contact lens which is proteinaceous deposit-free in an ophthalmically acceptable composition comprising an ophthalmically acceptable aqueous carrier component, an ophthalmically acceptable wearability component in an amount effective to enhance the wearability of said soaked contact lens in a mammalian eye, and an ophthalmically acceptable antioxidant component in an amount effective to inhibit the formation of at least one of proteinaceous deposits and lipid deposits on said soaked contact lens after said soaked contact lens is placed in a mammalian eye, said ophthalmically acceptable antioxidant component being selected from the group consisting of Vitamin A, Vitamin E, ascorbic acid, glutathione, oxidation-type glutathione, ophthalmically acceptable antioxidant salts thereof, ophthalmically acceptable antioxidant derivatives thereof, precursors thereof and mixtures thereof.

13. A composition useful for inhibiting the formation of deposits on a contact lens being worn in a mammalian eye comprising:

an ophthalmically acceptable aqueous carrier component;

an ophthalmically acceptable wearability component in an amount effective to enhance the wearability of a contact lens in a mammalian eye; and at least one ophthalmically acceptable antioxidant component in an amount in a range of about 0.001% to about 0.5% by weight per volume effective to inhibit the formation of at least one of proteinaceous deposits and lipid deposits on a proteinaceous deposit-free contact lens being worn in a mammalian eye, said composition being ophthalmically acceptable and having an ophthalmically acceptable pH greater than 5.0, said ophthalmically acceptable antioxidant component being selected from the group consisting of Vitamin A, Vitamin E, ascorbic acid, ophthalmically acceptable antioxidant salts thereof, ophthalmically acceptable antioxidant derivatives thereof, precursors thereof and mixtures thereof, said composition being ophthalmically acceptable.

14. The composition of claim 13 wherein said composition has a pH of less than about 8.0, and is free of enzymes and ionic surfactants.

15. The composition of claim 13 wherein said composition has a pH in the range of about 5.3 to about 6.0.

16. The composition of claim 13 wherein said ophthalmically acceptable wearability component includes a combination of an opthalmically acceptable surfactant component and an opthalmically acceptable conditioning component.

17. The composition of claim 15 which includes polyvinyl alcohol and polyvinyl pyrrolidone each in an amount effective to act to enhance the wearability of the contact lens in a mammalian eye.

18. The composition of claim 13 wherein said ophthalmically acceptable wearability component includes a combination of a polyoxyethylene, polyoxypropylene block polymer and propylene glycol alginate.

* * * * *